United States Patent [19]

Innami et al.

[11] Patent Number: 4,659,388

[45] Date of Patent: Apr. 21, 1987

[54] ADDITIVE COMPOSITION FOR FOODS OR DRUGS

[75] Inventors: Satoshi Innami, Tokyo; Yoshitaka Fukui, Himeji, both of Japan

[73] Assignee: Daicel Chemical Industries, Ltd., Sakai, Japan

[21] Appl. No.: 741,974

[22] Filed: Jun. 6, 1985

[30] Foreign Application Priority Data

Jun. 8, 1984 [JP] Japan ................................ 59-117504

[51] Int. Cl.[4] ............................ A23L 1/04; C08L 1/02
[52] U.S. Cl. ................................ 106/163.1; 426/573; 536/56; 514/781
[58] Field of Search ........................... 426/573; 536/56; 106/163.1

[56] References Cited

U.S. PATENT DOCUMENTS

| 3,023,104 | 2/1962 | Battista | 426/589 |
| 4,216,242 | 8/1980 | Braverman | 426/573 |
| 4,269,859 | 5/1981 | Morse | 536/56 |
| 4,336,370 | 6/1982 | Yasnovsky et al. | 536/58 |
| 4,341,807 | 7/1982 | Turbak et al. | 426/573 |
| 4,378,381 | 3/1983 | Turbak et al. | 426/573 |
| 4,385,172 | 5/1983 | Yasnovsky et al. | 536/56 |
| 4,391,973 | 7/1983 | Cruz | 536/56 |
| 4,452,722 | 6/1984 | Turbak et al. | 426/573 |
| 4,474,949 | 10/1984 | Chatterjee et al. | 536/56 |
| 4,543,410 | 9/1985 | Mamerto | 536/56 |

*Primary Examiner*—Ronald W. Griffin
*Attorney, Agent, or Firm*—Flynn, Thiel, Boutell & Tanis

[57] ABSTRACT

A food or drug is prepared to be suitable for treatment of intestinal disorders by adding thereto a composition which comprises microfibrillated cellulose and a water-soluble saccharide.

7 Claims, No Drawings

ADDITIVE COMPOSITION FOR FOODS OR DRUGS

FIELD OF THE INVENTION

This invention relates to a composition for foods and drugs which comprises microfibrillated cellulose (which will be referred to as MFC hereinbelow) which can be handled as a solid material, and a water soluble saccharide. The composition is effective in treating intestinal disorders.

DESCRIPTION OF PRIOR ARTS

MFC may be prepared by beating pulp in a viscous state in water according to the process disclosed in Japanese Patent Laid-Open No. 100801/1981. A high shear force applied under a high pressure would change the microstructure of cellulose fibers of the pulp to thereby effect microfibrillation. The cellulose thus obtained was defined as microfibrillated cellulose in the specification of the above-mentioned patent.

The MFC exhibits particular properties such as a remarkably high water retention, a stable dispersibility and suspendibility in water and high reactivities to various chemical reagents and enzymes. The MFC is usually obtained in the form of a suspension in water. When the suspension is dehydrated and dried, the fibrils agglomerate with each other and keratinize to thereby form a product which would be hardly dispersed or suspended in water when poured into water again.

It was found that the agglomeration of the fibrils might be caused by the formation of hydrogen bonding between MFC's. It was also found that a dry composition which is redispersible and resuspendible in water may be prepared by dehydrating and drying the MFC suspension in water in the presence of a substance having active hydrogen, such as a polyhydric alcohol. However the use of this dry composition has not been sufficiently developed as yet.

SUMMARY OF THE INVENTION

As a result of our researches to prepare a dry composition containing MFC by using water-soluble saccharide or sugar as the substance having active hydrogen, we have succeeded in obtaining a product which can be handled as a solid material and is redispersible and resuspendible in water. By examining the availability of the product as edible fiber, we have further found that it is more effective for treating intestinal disorders than conventional cellulose and is very useful in preparing foods and drugs to thereby complete the present invention. Thus the present invention provides a composition for foods and drugs which comprises 15 to 65% by weight of microfibrillated cellulose and 85 to 35% by weight of water-soluble saccharide and is effective in treating intestinal disorders.

The water-soluble saccharide used in the present invention together with MFC may be natural saccharides or water-soluble cellulose-derivatives, such as sucrose, pectin, guar gum, mannan, xanthane gum, carboxymethylcellulose, sodium alginate and hydroxyethylcellulose.

A powdery composition may be prepared by adding these water-soluble saccharides to MFC suspended in water at a ratio of from 85/15 to 35/65 on solid basis, mixing them and drying. When added to water, the powdery composition would be readily dispersed to give a stable aqueous suspension.

Effects

The powdery composition is smooth to the mouth touch and exhibits no imcompatibility. Thus the powdery composition may be added to food materials as such or in the form of a paste or a slurry by mixing it with an appropriate amount of water to prepare edible products.

Alternately, the powdery composition may be taken separately as a drug instead of as an additive to food. That is, the composition comprising MFC and water-soluble saccharide may be molded into tablets as such by directly tabletting depending on the kind of the water-soluble saccharide. Even when compression molding is impossible, the composition may be readily molded into tablets by adding conventional excipients such as lactose or microcrystalline cellulose. The tablets thus obtained may be taken as a drug which is effective in treating intestinal disorders.

PREFERRED EMBODIMENTS OF THE INVENTION

To further illustrate the present invention, and not by way of limitation, the following examples will be given.

REFERENTIAL EXAMPLE

Water was added to purified sulfite pulp (Alfania F; a product of Reyonier Co.) which contained 92 to 93% by weight of $\alpha$-cellulose and had a degree of polymerization of 1050 to 1070 to form a slurry. The slurry was passed cyclically 40 times under a high pressure (i.e. approximately 500 kg/cm) with a homogenizer (a product of Manton-Gaulin Co.) according to the process disclosed in Japanese Patent Laid-Open No. 100801/1981. The aqueous MFC suspension thus obtained exhibited a viscosity of 3000 to 6000 cps and a water retention of MFC (i.e. the water content determined after centrifuging at 1000 G for 10 min) of 1350%.

Various saccharides are added to the MFC suspension to give a ratio of 50/50 on solid basis and each mixture was dried at 60° to 110° C. for at least one hour under aeration to thereby prepare a dry MFC/saccharide composition. An undried MFC/saccharide composition sampled separately was adjusted to a solid concentration of 2% to determine the viscosity. Water was added to the dried MFC/saccharide composition to give a solid concentration of 2% and the mixture was stirred with a mixer at 10000 rpm for one min to redisperse the composition, thereby preparing a suspension. As shown in Table 1, the viscosities of the suspensions which had been dried and redispersed were similar to those of the undried suspensions.

TABLE 1

| | Viscosity of aqueous suspension of composition | |
|---|---|---|
| Composition | Undried | Dried and redispersed |
| MFC/pectin | 2300 | 1960 |
| MFC/isomerized lactose | 1360 | 820 |
| MFC/sucrose | 1390 | 1200 |

EXAMPLES AND COMPARATIVE EXAMPLES

Rats were fed with the dry MFC/saccharide compositions prepared in the Referential Example to examine the effects.

SD rats of five weeks of age and approximately 60 g of body weight were preliminarily fed with a standard feed for one week and then classified into six groups each composed of six rats. These rats were fed with either experimental (i.e. high cholesterol) or standard feeds shown in Table 2 for 14 days to determine their feed intake, body weight and amounts of feces.

Table 2 shows the prescription of each feed.

TABLE 2

| Ingredient | Standard | High cholesterol | High cholesterol/ pectin | High cholesterol/ composition |
|---|---|---|---|---|
| casein | 20.0 | 20.0 | 20.0 | 20.0 |
| mineral/vitamin mixture*1 | 4.5 | 4.5 | 4.5 | 4.5 |
| choline tartrate | 0.2 | 0.2 | 0.2 | 0.2 |
| cellulose powder*2 | 5.0 | 5.0 | | |
| cholesterol | | 0.5 | 0.5 | 0.5 |
| sodium bilate | | 0.25 | 0.25 | 0.25 |
| lard | 10.0 | 10.0 | 10.0 | 10.0 |
| sucrose | 60.3 | 59.55 | 59.55 | 54.55 |
| pectin | | | 5.0 | |
| composition*3 | | | | 10.0 |

Note:
*1mineral/vitamin mixture: AIN-76 TM (J. Nutr. 107, 1340 (1977)).
*2cellulose powder: Toyo Roshi Cellulose Powder D.
*3composition: MFC/saccharide = 50/50.

Changes in body weights of the rats are shown in Table 3.

TABLE 3

| | | Body weights of rats fed for 14 days | | |
|---|---|---|---|---|
| Comp. Ex. and Ex. | Feed | Initial g | Final g | Gain g/day |
| Comp. EX. 1 | standard | 114 ± 2 | 212 ± 3 | 7 |
| Comp. EX. 2 | high cholesterol (H.C.) | 114 ± 2 | 212 ± 6 | 7 |
| Comp. EX. 3 | H.C./pectin | 114 ± 2 | 199 ± 5 | 6 |
| Ex. 1 | H.C./composition*3 | 114 ± 2 | 214 ± 5 | 7 |
| Ex. 2 | H.C./composition*4 | 114 ± 2 | 212 ± 5 | 7 |
| Ex. 3 | H.C./composition*5 | 114 ± 2 | 218 ± 5 | 7 |

*3MFC/pectin = 50/50
*4MFC/isomerized lactose = 50/50
*5MFC/sucrose = 50/50

Table 4 shows a relationship between feed-intake and amount of feces.

TABLE 4

| | Feed intake and amount of feces (fed for 14 days) | | | | |
|---|---|---|---|---|---|
| | | | Amount of feces g/14 days | | |
| Comp. Ex. and Ex. | Feed-intake g/day | Feed efficiency g/day*6 | wet | dry | water |
| Comp. Ex. 1 | 17.5 | 0.42 | 19.6 | 18.2 | 1.5 |
| Comp. Ex. 2 | 16.7 | 0.42 | 17.7 | 14.8 | 2.9 |
| Comp. Ex. 3 | 15.7 | 0.39 | 15.8 | 13.0 | 2.8 |
| Ex. 1 | 17.6 | 0.42 | 43.1 | 31.7 | 11.4 |
| Ex. 2 | 16.6 | 0.42 | 43.2 | 27.7 | 15.5 |
| Ex. 3 | 17.4 | 0.43 | 27.7 | 22.8 | 5.0 |

*6feed efficiency = body weight gain/feed intake.

EFFECTS OF THE INVENTION

The results of these experiments show that the addition of the MFC/saccharide compositions to feeds would result in a remarkable increase in the amount of feces while scarcely affecting feed intake and body weight gain. Both of dry weight and water content of feces increased. These facts suggest that feces of the groups administered MFC/sugar compositions might have a high water retention. These effects were higher than those of cellulose powder and pectin which is a hardly digestible saccharide. Taking into account the fact that an MFC composition was added in an amount of only 10% of the feed, the remarkable increase in feces and its water retention might result from a synergetic effect of MFC and saccharides in treating intestinal disorders. Thus it suggests that the composition of the present invention is very useful for foods and drugs.

The embodiments of the invention in which an exclusive property or privilege is claimed are defined as follows:

1. A dry solid composition suitable for use as a food and drug additive or for treating intestinal disorders, consisting essentially of (1) from 15 to 65 percent by weight of microfibrillated cellulose and (2) from 85 to 35 percent by weight of a water-soluble saccharide effective to prevent agglomeration of the fibrils of said microfibrillated cellulose.

2. A dry solid composition as claimed in claim 1 which is in the form of a powder.

3. A dry solid composition as claimed in claim 1 which is in the form of a tablet for oral administration for treating intestinal disorders.

4. A dry solid composition as claimed in claim 1 which has been prepared by drying an aqueous suspension of said microfibrillated cellulose and containing said water-soluble saccharide.

5. A dry solid composition as claimed in claim 1 in which said water-soluble saccharide has an active hydrogen atom in the molecule.

6. A dry solid composition as claimed in claim 1 in which said water-soluble saccharide is selected from the group consisting of sucrose, pectin, guar gum, mannan, xanthane gum, carboxymethylcellulose, sodium alginate and hydroxyethylcellulose.

7. A dry solid composition as claimed in claim 1 in which said water-soluble saccharide is selected from the group consisting of pectin, isomerized lactose and sucrose.

* * * * *